United States Patent [19]

Pearson et al.

[11] Patent Number: 4,904,301

[45] Date of Patent: Feb. 27, 1990

[54] 5-FLUOROMETHYL-1,2,4-TRIAZOLO(1,5-A)-PYRIMIDINES

[75] Inventors: Norman R. Pearson, Walnut Creek; William A. Kleschick, Martinez, both of Calif.; Chrislyn M. Carson, Midland, Mich.

[73] Assignee: The Dow Chemical Company, Midland, Mich.

[21] Appl. No.: 183,570

[22] Filed: Apr. 19, 1988

[51] Int. Cl.$^4$ .................. A01N 43/90; C07D 487/04
[52] U.S. Cl. ......................................... 71/92; 544/263
[58] Field of Search .............................. 544/263; 71/92

[56] References Cited

U.S. PATENT DOCUMENTS

| | | | |
|---|---|---|---|
| 3,637,366 | 1/1972 | Wietelmann et al. | 71/92 |
| 3,920,690 | 11/1975 | Harrington et al. | 548/358 |
| 3,923,810 | 12/1975 | Harrington et al. | 544/381 |
| 4,349,378 | 9/1982 | Cliff et al. | 71/103 |
| 4,818,273 | 4/1989 | Kleschik et al. | 71/90 |

FOREIGN PATENT DOCUMENTS

| | | |
|---|---|---|
| 142152A | 5/1985 | European Pat. Off. . |
| 58-31894R | 10/1973 | Japan . |
| 951652 | 3/1964 | United Kingdom . |

OTHER PUBLICATIONS

Broadbent et al., J. Chem. Soc., 1965, pp. 3369–3372.
Okabe et al., J. Fac. Agr., Kyushu Univ., 19, 91–102, (1975).
Okabe et al., J. Heterocyclic Chemistry, 20, 735, (1983).
Novinson et al., J. Med. Chem., 25, pp. 420–426.

*Primary Examiner*—Mukund J. Shah
*Assistant Examiner*—C. L. Cseh
*Attorney, Agent, or Firm*—D. Wendell Osborne

[57] ABSTRACT

N-(Substituted-phenyl)-5-fluoromethyl-1,2,4-triazolo[1,5-a]pyrimidine-2-sulfonamides are prepared from 2-benzylthio-5-fluoromethyl-1,2,4-traizolo[1,5-a]pyrimidines and found to to be herbicidal. The compounds, illustrated by 5-fluoromethyl-7-methoxy-(2,6-dichloro-3-methylphenyl)-1,2,4-triazolo[1,5-a]pyrimidine-2-sulfonamide, are degradable in the soil.

7 Claims, No Drawings

5-FLUOROMETHYL-1,2,4-TRIAZOLO(1,5-A)-PYRIMIDINES

The usefulness of herbicides for the control of unwanted vegetation in crops is greatly reduced when the herbicide does not dissipate in the environment at a sufficiently rapid rate that it is effectively not present when succeeding crops are planted. This is particularly true when the succeeding crop is highly susceptible to the herbicide. For this reason compounds possessing good herbicidal effectiveness that are, in addition, readily degradable in the soil are especially valuable.

The substituted 1,2,4-triazolo[1,5-a]pyrimidine-2-sulfonamides disclosed in European Application No. 0142152A published May 22, 1985, are known to be herbicidal, to be especially phytotoxic to certain broadleaf weeds, and to possess selectivity toward crops, such as wheat, rice, corn, soybeans, and cotton. Many of these compounds are, however, relatively persistent in the soil. As a consequence they often cannot be used where soil degradation is not sufficiently fast to preclude excessive carry-over from one crop to another, especially where the succeeding crop is a relatively susceptible crop.

SUMMARY OF THE INVENTION

It has now been found that 1,2,4-triazolo[1,5-a]pyrimidine-2-sulfonamides possessing a fluoromethyl substituent in the 5-position of the triazolo[1,5-a]pyrimidine ring are markedly more degradable in the soil than are related compounds possessing other substituents, and, in addition, are outstanding selective herbicides for use in controlling unwanted vegetation in many crops. In particular, 5-fluoromethyl-1,2,4-triazolo[1,5-a]pyrimidine-2-sulfonamide compounds of Formula I

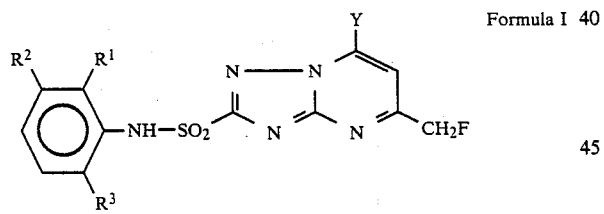

Formula I wherein
Y represents H, $CH_3$, $C_2H_5$, $OCH_3$, or $SCH_3$;
$R^1$ represents H, F, Cl, Br, $CH_3$, $CF_3$, $NO_2$, $CO_2(C_1-C_4)$alkyl, or $CON(C_1-C_4)$alkyl$_2$;
$R^2$ represents H or $CH_3$; and
$R^3$ represents F, Cl, Br, $NO_2$, $CO_2(C_1-C_4)$alkyl, $CON(C_1-C_4)$alkyl$_2$, $OCH_3$, or $OC_2H_5$;
with the proviso that $R^1$ and $R^3$ are not simultaneously $NO_2$, $CO_2(C_1-C_4)$alkyl, or $CON(C_1-C_4)$alkyl$_2$;

and agriculturally acceptable salts thereof are soil degradable herbicides that can be used in situations where crops are rotated. They are especially useful for the control of unwanted vegetation in cotton and wheat and can be used in many other crops.

The 5-fluoromethyl-1,2,4-triazolo[1,5-a]pyrimidine moiety containing intermediates utilized in the preparation of the compounds of Formula I, which are depicted by Formula II

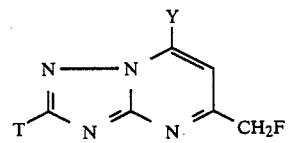

Formula II wherein
Y represents H, Cl, OH, $CH_3$, $C_2H_5$, or $OCH_3$, and
T represents HS, $(C_2-C_4)$alkylthio, benzylthio, or $ClSO_2$
are an integral part of the invention as are intermediates of Formula I wherein Y represents OH or Cl.

DETAILED DESCRIPTION OF THE INVENTION

The biodegradable herbicides of the present invention are those of Formula 1 in which Y represents hydrogen, methyl, ethyl, methoxy or methylthio and $R^1$, $R^2$, and $R^3$ represent a variety of substituents as defined in the Summary of the Invention. Specific examples include 5-fluoromethyl-N-(2,6-dichlorophenyl-1,2,4-triazolo[1,5-a]pyrimidine-2-sulfonamide, 5-fluoromethyl-7-methyl-N-(2,6-dichloro-3-methylphenyl)-1,2,4-triazolo[1,5-a]pyrimidine-2-sulfonamide, 5-fluoromethyl-7-methoxy-N-(2,6-difluoro-3-methylphenyl)-1,2,4-triazolo[1,5-a]pyrimidine-2-sulfonamide, and 5-fluoromethyl-7-methylthio-N-(2methoxy-6-(trifluoromethyl)phenyl)-1,2,4-triazolo1,5-a]pyrimidine-2-sulfonamide. Compounds in which Y represents hydrogen, methoxy or methylthio are preferred as are compounds in which $R^1$ represents chloro, fluoro, bromo, or trifluoromethyl and $R^3$ represents chloro, fluoro, bromo, or methoxy. Compounds in which $R^2$ represents methyl are additionally preferred.

The term "agriculturally acceptable salts" is employed herein to denote compounds wherein the acidic sulfonamide proton of the compound of Formula I is replaced by a cation which is not herbicidal, especially to crop plants, nor significantly deleterious to the applicator, the environment, or the ultimate user of any crop being treated. Suitable cations include, for example, those derived from alkali or alkaline earth metals and those derived from ammonia and amines. Preferred cations include sodium, potassium, magnesium, and aminium cations of the formula

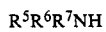

$R^5R^6R^7NH$ wherein $R^5$, $R^6$, and $R^7$ each, independently represents hydrogen or $C_1-C_{12}$ alkyl, $C_3-C_{12}$ cycloalkyl, or $C_3-C_{12}$ alkenyl, each of which is optionally substituted by one or more hydroxy, $C_1-C_8$ alkoxy, $C_1-C_8$ alkylthio or phenyl groups. Additionally, any two of $R^5$, $R^6$, and $R^7$ together may represent an aliphatic difunctional moiety containing 1 to 12 carbon atoms and up to two oxygen or sulfur atoms. Salts of the compounds of Formula I can be prepared by treatment of compounds of Formula I with a metal hydroxide, such as sodium hydroxide, potassium hydroxide, or magnesium hydroxide, or an amine, such as ammonia, trimethylamine, hydroxyethylamine, bisallylamine, 2-butoxyethylamine, morpholine, cyclododecylamine, or benzylamine.

The terms alkyl, alkenyl, alkoxy and alkylthio as used herein includes straight chain and branched chain moieties. Thus, typical alkyl groups are methyl, ethyl, 1- methylethyl, 1,1-dimethyl-ethyl, propyl, 2-methylpropyl, 1-methylpropyl, and butyl.

The compounds of the present invention can be prepared by the appropriate general methods disclosed in European Application No. 0142152A. For example, a 4-fluoroacetoacetate ester can be combined with a 5-mercapto-, 5-alkylthio-, or 5-benzylthio-3-amino-1,2,4-triazole in refluxing glacial acetic acid and allowed to react for several hours. The crystals that form on cooling can be collected and dried to obtain a compound of Formula II wherein Y represents OH and T represents HS, ($C_2$-$C_4$)alkylthio, or benzylthio. Treatment of this intermediate with excess refluxing phosphorus oxychloride for several hours and distilling the excess phosphorus oxychloride from the mixture produces a reaction mixture which can be dissolved in a water immiscible solvent, such as methylene chloride, and then contacted with water. Removal of the solvent leaves a compound of Formula II wherein Y represents Cl and T is unchanged. The Y moiety in this intermediate can be converted to methoxy when T represents $C_2$-$C_4$ alkylthio or benzylthio by allowing the intermediate to stand in a solution of methanol containing about an equimolar quantity of sodium methoxide.

In a similar manner, intermediates of Formula II in which Y represents hydrogen, methyl, or ethyl and T represents mercapto, alkylthio, or benzylthio can be prepared by condensation or a 1,3-dicarbonyl compound of the formula $RC(O)CH_2C(O)CH_2F$ wherein R represents hydrogen, methyl, or ethyl with a 5-mercapto-, 5-alkyl, or 5-benzyl-2-amino-1,2,4-triazole in refluxing glacial acetic acid. The two isomers that may form can be separated by conventional means, such as liquid-liquid chromatography or fractional crystallization.

Treatment of intermediates of Formula II wherein T represents mercapto, $C_2$-$C_4$ alkylthio, or benzylthio with chlorine in mixture of a water immiscible, unreactive solvent, such as chloroform, and water or in aqueous acetic acid at about 0° C. leads to 2-chlorosulfonyl-1,2,4-triazolo[1,5-a]pyrimidine intermediates of Formula II (T represents chlorosulfonyl). These intermediates can be recovered by conventional means.

2-Chlorosulfonyl-1,2,4-triazolo[1,5-a]pyrimidines can be condensed with appropriately substituted anilines as described in European Application No. 0142152A to obtain the biodegradable herbicides of the present invention. It is often, however, preferred to condense them with an appropriately substituted N-trialkylsilylylaniline (typically, trimethyl or triethyl) essentially as described in application Ser. No. 118,495, filed Nov. 9, 1987. In this procedure the compound of Formula II wherein T represents $ClSO_2$ and the appropriately substituted N-trialkylsilylaniline are combined in an organic solvent, such as acetonitrile, containing a catalyst, such as dimethyl sulfoxide, and allowed to react at ambient temperature for several hours. The reaction mixture is contacted with an aqueous reagent often after replacing the reaction solvent with a water-immiscible solvent, such as methylene chloride. The desired product can b recovered from the resulting mixture by conventional means, such as by evaporation of the solvents or by addition of a miscible solvent in which the product is not soluble, such as hexane.

Compounds of Formula I in which Y represents methoxy or methylthio can be prepared from compounds of Formula I in which Y represents chloro by combining the latter with about two moles of sodium methoxide in methanol or sodium methanethiolate in an alcohol. The reactions proceed readily at ambient temperature or with cooling. The products can be recovered by adding an acid, such as acetic acid, and water, and, if desired, can be purified by conventional means.

5-Mercapto-, 5-alkylthio-, and 5-benzylthio-3-amino-1,2,4-triazoles and the substituted anilines required for the preparation of the herbicides and intermediates of the present invention are known in the art. The substituted N-trialkylsilylanilines can be prepared by the reaction of the correspondingly substituted anilines with a trialkylsilyl halide, such as trimethylsilyl bromide or triethylsilyl chloride, and a tertiary amine base in an anhydrous, inert organic solvent using the general procedures described in the journal *Synthesis*, 1981, 368–9. The substituted N-trialkylsilylanilines obtained can be purified by distillation.

The herbicides of the present invention degrade surprisingly rapidly in most agricultural soils, a property conferred upon them by the presence of the 5-fluoromethyl substituent. Thus, whereas typical substituted 1,2,4-triazolo[1,5-a]pyrimidine-2-sulfonamide herbicides have half-lives in moist sandy loam soil with moderate amounts of soil organic matter at growing season temperatures of greater than about 30 days and as a result can remain in the soil in deleterious amounts from one crop planting until the next, the selected herbicides of the present invention have half-lives of less than 30 days and often less than two weeks under the same conditions. Compounds of the present invention wherein Y represents hydrogen, methoxy, or methylthio are especially readily degraded in the soil, having half-lives of about 6 to about 20 days. Such compounds are preferred because the threat of carry-over is further reduced when compounds having half-lives of less than 21 days are employed. Because of their degradation, the 5-fluoromethyl compounds of the present invention do not generally remain in the soil in deleterious amounts from one crop planting until the next when applied at typical herbicide rates and, especially at typical selective herbicide rates. The degradation appears to be mainly biological in nature.

The phenomenon of degradation of a herbicide in the soil is influenced by not only the chemical and physical nature of a herbicide, but also the nature of the soil, the climatic conditions, and the previous use of the soil. Accordingly, degradation rates must be viewed as ranges, rather than as specific numbers. A discussion of the phenomenon can be found in "*Herbicides: Physiology, Biochemistry, Ecology*", Volume 2, by L. J. Audus. Most agricultural soils are located in temperate climates, experience considerable rainfall (or are irrigated), are used for agriculture in a continuous way, and have considerable capability to degrade synthetic organic chemicals. Herbicides having half-lives of greater than about a month, however, are known to have varying degrees of carry-over problems in typical agricultural soils found in temperate climates. Herbicides having half-lives of less than about one month are generally free of such problems in most circumstances. Typical agricultural soils in temperate climates contain clay and sand or silt, about 10 to about 30 percent water, and about 0.5 to about 8 percent organic matter. The average temperature ranges from about 21° to about 32° C. during growing seasons and about 0° to about 21° C. during off-seasons.

The 5-fluoromethyl-1,2,4-triazolo[1,5-a]pyrimidine-2-sulfonamide herbicides of the present invention are useful for the control of unwanted vegetation in valuable crops when applied at selective rates, especially in postemergence applications. The control of unwanted vegetation in wheat and cotton crops is especially important, but selectivity is observed in some instances for barley, soybeans and other grassy and broadleaf crops. Selectivity is a function of not only the chemical and physical nature of a herbicide, but also the method of application, the variety of the crop plant, the specific weeds present, the climatic conditions of temperature and humidity, the soil type and condition (for preemergence applications), and other factors. The compounds of the present invention are selective to wheat and cotton and to other crops under most circumstances, particularly in postemergence applications, but certain circumstances may be contra-indicated for some of the compounds. These will be readily apparent to those skilled in the art using the general precepts of herbicidal action and the teachings herein. Compounds of Formula I wherein $R^2$ represents methyl are often especially selective. The compounds of the present invention are useful as general herbicides at application rates greater than the selective rates.

General herbicide action is usually observed for compounds of Formula I at rates of greater than about 100 g/Ha for either preemergence or postemergence applications. The selective control of susceptible weeds in cotton can generally be accomplished at application rates of about 1 g/Ha to about 60 g/Ha and in wheat at rates of about 1 g/Ha to about 150 g/Ha. An appropriate rate for each crop, compound and circumstance can be determined by simple range finding tests using the teachings herein.

The term "herbicide" is used herein to mean an active ingredient which controls or adversely modifies growth of plants. By "growth controlling" or "herbicidally effective" amount is meant an amount of active ingredient which causes an adversely modifying effect and includes deviations from natural development, killing, regulation, dessication, retardation, and the like. The terms "plants" and "weeds" are meant to include germinant seeds, emerging seedlings and established vegetation.

The compounds of the present invention can be used directly as herbicides, but it is generally preferable to first prepare a herbicidal composition containing one or more of the compounds in combination with an agriculturally acceptable adjuvant or carrier. Suitable adjuvants or carriers should not be phytotoxic to valuable crops, particularly at the concentrations employed in applying the compositions for selective weed control in the presence of crops, and should not react chemically with compounds of Formula I or other composition ingredients. Such mixtures can be designed for application directly to plants or their locus or can be concentrates or formulations which are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, isopropyl alcohol, amyl alcohol, ethylene glycol, propylene glycol, glycerine, and the like. Water is generally the carrier of choice for the dilution of concentrates.

Suitable solid carriers include talc, pyrophyllite clay, silica, attapulgus clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is frequently desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Typical surface active agents include salts of alkyl sulfates, such as diethanolammonium lauryl sulfate; alkylarylsulfonate salts, such as calcium dodecylbenzenesulfonate; alkylphenolalkylene oxide addition products, such as nonylphenol-$C_{18}$ ethoxylate: alcohol-alkylene oxide addition products, such as tridecyl alcohol-$C_{16}$ ethoxylate; soaps, such as sodium stearate: alkylnaphthalenesulfonate salts, such as sodium dibutylnaphthalenesulfonate: dialkyl esters of sulfosuccinate salts, such as sodium di(2-ethylhexyl) sulfosuccinate: sorbitol esters, such as sorbitol oleate: quaternary amines, such as lauryl trimethylammonium chloride: polyethylene glycol esters of fatty acids, such as polyethylene glycol stearate: block copolymers of ethylene oxide and propylene oxide: and salts of mono and dialkyl phosphate esters.

Other adjuvants commonly utilized in agricultural compositions include antifoam agents, compatibilizing agents, sequestering agents, neutralizing agents and buffers, corrosion inhibitors, dyes, odorant, penetration aids, spreading agents, sticking agents, dispersing agents, thickening agents, freeze point depressants, antimicrobial agents, and the like. The addition of crop oil and crop oil concentrates is typical. The compositions can also contain other compatible components, for example, other herbicides, plant growth regulants, fungicides, insecticides, and the like and can be formulated with solid, particulate fertilizer carriers such as ammonium nitrate, urea and the like or with liquid fertilizers.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to plants or their locus generally contain about 0.001 to about 5 weight percent active ingredient and preferably contain about 0.01 to about 1.0 percent.

The present compositions can be applied by the use of conventional ground or aerial dusters and sprayers, by addition to irrigation water, and by other conventional means known to those skilled in the art.

The following examples are presented to illustrate the invention and should not be interpreted as limiting the scope.

EXAMPLE 1

Preparation of t-Butyl 4-Fluoroacetoacetate

A solution containing 12.6 g (125 mmol) of diisopropylamine in 90 ml of dry tetrahydrofuran was cooled to −78° C. and 52.4 ml of 2.5 M n-butyllithium (131 mmol) was added. A solution of 14.5 g (125 mmol) of t-butyl acetate in 10 ml of tetrahydrofuran was then added dropwise over a 30 min period with stirring and allowed to react for another 30 min at −78° C. A solution of 6.00 g (56.6 mmol) of ethyl fluoroacetate in tetrahydrofuran was added dropwise with stirring to the resultant pale yellow solution and the mixture allowed to react for another 30 min at −78° C. and then allowed to stir and warm to ambient temperature over one hour. The resulting pale yellow solution was diluted with 250 ml of ether and the ethereal solution was extracted with 250 ml of 1 N HCl, 250 ml of water, and 250 ml of saturated aqueous sodium bicarbonate. The solution was then dried over magnesium sulfate and distilled at atmospheric pressure to remove the solvents. The residue was fractionally distilled under reduced pressure from a based-washed and oven-dried flask containing a few potassium bicarbonate crystals to obtain 7.00 g (70 percent of theory) of the desired product as a colorless oil boiling at 72°–74° C. at 10 torr. The proton and fluorine nmr spectra were consistent with the assigned structure.

EXAMPLE 2

Preparation of 2-Benzylthio-5-fluoromethyl-7-hydroxy-1,2,4-triazolo1,5-a]pyrimidine A solution containing 20.0 g (114 mmol) of t-butyl 4-fluoroacetoacetate, 23.4 g (114 mmol) of 3-amino-5-benzylthio-1,2,4-triazole in 250 ml of glacial acetic acid was heated at reflux with stirring for 5.5 hr and then allowed to cool and stand overnight. The crystals that formed were ground to reduce their size and then recovered by filtration and dried in a vacuum oven to obtain 18.3 g (55 percent of theory) of the title product as a white powder melting with decomposition at 214°–218° C.

Elemental Analysis:
Calc. for $C_{13}H_{11}FN_4OS$: %C, 53.79; %H, 3.82: %N, 19.29
Found: %C, 53.35; %H, 3.98; %N, 19.00

EXAMPLE 3

Preparation of 2-Benzylthio-5-fluoromethyl-7-chloro-1,2,4-triazolo[1,5-a]pyrimidine A mixture of 17.0 g (58.6 mmol) of 2-benzylthio-5-fluoromethyl-7-hydroxy-1,2,4-triazolo[1,5-a]pyrimidine and 100 ml of phosphorus oxychloride was heated at reflux for three hours and was then concentrated by simple distillation using a water aspirator to reduce the pressure to obtain a dark, viscous oil. This was dissolved in 300 ml of methylene chloride and treated cautiously with stirring with 200 ml of water. The mixture was stirred vigorously for 30 min. at ambient temperature and then allowed to separate into phases. The organic phase was separated, washed with water and saturated aqueous sodium bicarbonate, dried over magnesium sulfate, and concentrated by evaporation under reduced pressure to obtain a dark oil. This solidified on trituration in hexane containing a little methylene chloride to yield 12.2 g (67 percent of theory) of the title compound as a tan solid melting at 81°–86° C.

Elemental Analysis:
Calc. for $C_{13}H_{10}ClFN_4S$: % C, 50.57: % H, 3.27; % N, 18.14
Found: % C, 51.14: % H, 3.31: % N, 18.33

EXAMPLE 4

Preparation of 5-Fluoromethyl-7-chloro-1,2,4-triazolo1,5-a]pyrimidine-2-sulfonyl chloride A solution containing 10.0 g (32.4 mmol) of 2-benzylthio-5-fluoromethyl-7-chloro-1,2,4-triazolo[1,5-a]pyrimidine in 100 ml of methylene chloride was combined with 100 ml of water and the mixture was cooled to 0°–5° C. Gaseous chlorine was passed into the mixture for 45 min. with vigorous stirring and cooling so as to maintain a temperature of less than 8° C. The disappearance of starting material was monitored by reverse phase HPLC. The cold mixture was allowed to react for another 15 min. and then the phases were allowed to separate and the organic phase was removed, washed with water and aqueous sodium bisulfite, and dried over magnesium sulfate. The solvent was removed by evaporation to obtain the title compound as an oil, which on trituration in hexane containing a little methylene chloride solidified to a light brown powder that, after being collected and dried, amounted to 7.1 g (77 percent of theory) and melted at 92°–98° C. The proton and fluorine nmr spectra were compatible with the assigned structure.

EXAMPLE 5

Preparation of 5-Fluoromethyl-7-methoxy-N-(2,6-dichlorophenyl)-1,2,4-triazolo[1,5-a]pyrimidine-2-sulfonamide A solution containing 3.08 g (13.1 mmol) of N-trimethylsilyl-2,6-dichloroaniline and 1.50 g (5.26 mmol) of 5-fluoromethyl-7-chloro-1,2,4-triazolo1,5-a]pyrimidine-2-sulfonyl chloride in 15 ml of dry acetonitrile was prepared and 0.075 ml (1.05 mmol) of dimethyl sulfoxide was added with stirring at ambient temperature. The mixture was allowed to react over 4 days and the resulting brown solution was then diluted with 150 ml of methylene chloride, washed with water, and dried over magnesium sulfate. The solvent was removed by evaporation under reduced pressure and replaced with hexane to obtain, after collection of the solids and drying, 1.80 g (84 percent of theory) of the 7-chloro analog of the title compound in about 80 percent purity. This was dissolved in 25 ml of dry methanol, the solution cooled to 0°–5° C. and a mixture of 1.70 g (7.89 mmol) of 25 weight percent sodium methoxide in methanol and 5 ml of methanol was added dropwise with stirring over a 10 min. period. The mixture was allowed to react for 10 min. and then about 1 ml of acetic acid was added. The solid that formed was collected, washed with methanol and with water, and dried to obtain 1.15 g (54 percent of theory) of the title compound as a light brown solid. This was extracted by stirring in boiling methanol, cooling, collecting the solids, and drying to obtain 1:09 g of product melting at 189°–191° C. The proton and fluorine nmr spectra were compatible with the assigned structure.

Elemental Analysis:
Calc. for $C_{13}H_{10}Cl_2FN_5O_3S$: % C, 38.44; % H, 2.48; % N, 17.23

Found: % C, 38.22: % H, 2.70; % N, 16.88

The following compounds were prepared in a similar way and found to have elemental analyses (C,H,N) and proton and fluorine nmr spectra compatible with the assigned structures:

5-Fluoromethyl-7-methoxy-N-(2,6-difluorophenyl)-1,2,4-triazolo[1,5-a]pyrimidine-2-sulfonamide, m.p. 161°–165° C.(dec):

5-Fluoromethyl-7-methylthio-N-(2,6-dichlorophenyl)-1,2,4-triazolo1,5-a]pyrimidine-2-sulfonamide, m.p. 263°–265° C.(dec):

5-Fluoromethyl-7-methoxy-N-(2-methoxy-6-(trifluoromethyl)phenyl)-1,2,4-triazolo[1,5-a]pyrimidine-2-sulfonamide, m.p. 170°–172° C.;

5-Fluoromethyl-7-methoxy-N-(2,6-dibromophenyl)-1,2,4-triazolo[1,5-a]pyrimidine-2-sulfonamide, m.p. 184°–186° C.:

5-Fluoromethyl-7-methylthio-N-(2,6-dibromophenyl)-1,2,4-triazolo[1,5-a]pyrimidine-2-sulfonamide, m.p. 241°–243° C. (dec):

5-Fluoromethyl-7-methoxy-N-(2,6-dichloro-3-methylphenyl)-1,2,4-triazolo[1,5-a]pyrimidine-2-sulfonamide, m.p. 198°–201° C.:

5-Fluoromethyl-N-(2,6-difluorophenyl)-1,2,4-triazolo[1,5-a]pyrimidine-2-sulfonamide, m.p. 215°–218° C.(dec) (by reduction with sodium cyanoborohydride).

The following additional compounds can be prepared similarly:

5-Fluoromethyl-7-methoxy-N-(2-carboxymethyl-6-methyl(phenyl)-1,2,4-triazolo[1,5-a]pyrimidine-2-sulfonamide;

5-Fluoromethyl-7-methoxy-N-(2-methyl-6-nitrophenyl)-1,2,4-triazolo1,5-a]pyrimidine-2-sulfonamide;

5-Fluoromethyl-7-methylthio-N-(2-methyl-6-nitrophenyl)-1,2,4-triazolo[1,5-a]pyrimidine-2-sulfonamide;

5-Fluoromethyl-7-methoxy-N-(2-dimethylcarboxamido-6-fluorophenyl)-1,2,4-triazolo[1,5-a]pyrimidine-2-sulfonamide;

5-Fluoromethyl-7-methoxy-N-(2-bromophenyl)-1,2,4-triazolo[1,5-a]pyrimidine-2-sulfonamide;

5-Fluoromethyl-7-methoxy-N-(2,3-dimethyl-6-nitrophenyl)-1,2,4-triazolo[1,5-a]pyrimidine-2-sulfonamide;

5-Fluoromethyl-7-methyl-N-(2,3-dimethyl-6-carboxybutylphenyl)-1,2,4-triazolo[1,5-a]pyrimidine-2-sulfonamide;

5-Fluoromethyl-7-methyl-N-(2-fluoro-6-(trifluoromethyl)phenyl)-1,2,4-triazolo[1,5-a]pyrimidine-2-sulfonamide;

5-Fluoromethyl-7-ethyl-N-(2-methoxy-6-methylphenyl)-1,2,4-triazolo[1,5a]pyrimidine-2-sulfonamide;

5-Fluoromethyl-N-(2-chloro-6-fluorophenyl)-1,2,4-triazolo1,5-a]pyrimidine-2-sulfonamide.

EXAMPLE 6

Postemergence Herbicidal Activity

Compounds of Formula I were dissolved in 14 ml acetone and 1 ml of dimethyl sulfoxide at one half of the most concentrated desired application concentration and the resulting solution was combined with 15 ml of an aqueous mixture containing about 20 percent isopropyl alcohol, about 2 percent Atplus ® 411F crop oil concentrate, and about 0.04 percent Triton ® X-155 surfactant. Solutions containing lower concentrations were prepared by diluting this mixture with a solution containing equal parts of a mixture of the second component described above and acetone containing 3 percent dimethyl sulfoxide. The solutions of known concentration were sprayed evenly onto various greenhouse-grown plant species in approximately the 2–4 leaf stage by means of a hand sprayer so as to obtain total coverage. The treated plants and control plants were placed in a greenhouse and held under conditions conducive to growth. After 13 days the percentage of control compared to the untreated plants was determined visually. Representative compounds tested, application rates employed, plant species tested, and results are given in Table 1.

TABLE I

POSTEMERGENCE HERBICIDAL ACTIVITY, PERCENT CONTROL

| Y | R¹ | R² | R³ | Dose Rate, PPM | Cotton | Wheat | Coffee Weed | Cocklebur | Jimson-weed | Lamium | Morning-glory | Pigweed | Velvet-leaf | Wild Buckwheat | Barnyard Grass | Johnson-grass |
|---|---|---|---|---|---|---|---|---|---|---|---|---|---|---|---|---|
| OCH₃ | Cl | H | Cl | 125 | 100 | 100 | 100 | 100 | 100 | 100 | 100 | 100 | 100 | 100 | 95 | 100 |
| OCH₃ | F | H | F | 15.6 | 10 | 85 | 85 | 40 | 70 | 90 | 70 | 100 | 80 | 100 | 70 | 100 |
| OCH₃ | CF₃ | H | OCH₃ | 125 | 50 | 100 | 100 | 100 | 100 | 100 | 100 | 100 | 100 | 100 | 90 | 100 |
| OCH₃ | Br | H | Br | 15.6 | 0 | 90 | 90 | 100 | 100 | 80 | 70 | 80 | 70 | 70 | 75 | 100 |
|  |  |  |  | 62.5 | 100 | 100 | 100 | 100 | 100 | 95 | 90 | 100 | 100 | 100 | 90 | 100 |
|  |  |  |  | 3.9 | 70 | 50 | 50 | 50 | 90 | 95 | 70 | 80 | 80 | 90 | 60 | 90 |
| OCH₃ | Cl | CH₃ | Cl | 125 | 65 | 100 | 100 | 100 | no test | 100 | 100 | 100 | 90 | 100 | 100 | 100 |
|  |  |  |  | 15.6 | 0 | 90 | 90 | 80 | no test | 100 | 70 | 100 | 70 | 100 | 70 | 85 |
|  |  |  |  | 62.5 | 20 | 75 | 80 | 100 | 100 | 100 | 100 | 100 | 100 | 100 | 0 | 70 |
|  |  |  |  | 7.8 | 0 | 8 | 0 | 80 | 80 | 100 | 70 | 100 | 90 | 100 | 0 | 30 |
| H | F | H | F | 125 | 80 | 55 | 0 | 100 | 100 | 100 | 80 | 100 | 100 | 80 | 20 | 60 |
|  |  |  |  | 15.6 | 0 | 30 | 0 | 80 | 100 | 50 | 0 | 90 | 70 | no test | 80 | 50 |
| SCH₃ | Cl | H | Cl | 62.5 | 90 | 70 | 100 | 100 | 100 | 100 | 80 | 100 | 80 | 90 | 50 | 80 |
| SCH₃ | Br | H | Br | 125 | 70 | 100 | 100 | 100 | no test | 100 | 100 | 100 | 80 | 100 | 100 | 100 |
|  |  |  |  | 15.6 | 15 | 60 | 100 | 30 | no test | 60 | 40 | 70 | 30 | 100 | 0 | 0 |

EXAMPLE 7

Preemergence Herbicidal Activity

Compounds of Formula I were dissolved in 15 ml of acetone at one half of the most concentrated desired application concentration and the resulting solution was combined with an equal volume of water containing 0.1 percent of Tween ® 20 surfactant. Solutions containing lower concentrations were prepared by diluting this with additional aqueous surfactant solution. The seeds of a number of species of plants were planted in beds containing a loam agricultural soil and, after planting, pre-determined amounts of the herbicide mixtures were sprayed on the soil surface and watered in to achieve the desired application rates. These and untreated control plants were then placed in a greenhouse under conditions conducive to germination and growth for a period of 14 days at which time a visual assessment was made of the reduction in stand and growth for the treated plants as compared to the control plants. Representative compounds tested, application rates employed, plant species tested, and results are given in Table II.

ter and allowed to stand overnight at ambient temperature to equilibrate. Duplicate treatments were made for each concentration and sample time interval desired. Six replicates were incubated in a 90–100 percent humidity room at about 27° C. and the other six, the controls, were frozen. After appropriate time periods, the cups were removed, planted with seven sunflower seeds (hybrid no. 3) as an indicator plant, and mulched with a very sandy soil. The cups were placed in a greenhouse under conditions conducive to germination and growth for 12–15 days. The plastic cups were then removed and the root growth evaluated visually on a scale of 0 to 20 wherein ratings are given as follows:

0 = no root penetration of the treated soil;
1 = up to 0.5 in. root penetration into treated soil;
5 = root penetration to the bottom of the treated soil including those with some slight bending at the bottom;
10 = root penetration to the bottom of the treated soil with a loose network of roots at the bottom:
20 = root penetration so as to form roots throughout the soil mass and covering the bottom.

A phytotoxicity index for each incubated treatment,

TABLE II

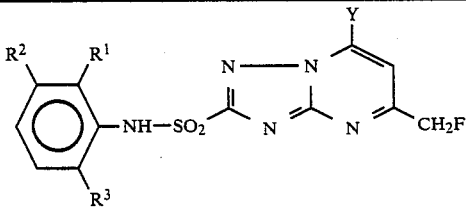

PREEMERGENCE HERBICIDAL ACTIVITY, PERCENT CONTROL

| Y | $R^1$ | $R^2$ | $R^3$ | Dose Rate, g/Ha | Cotton | Wheat | Curly Dock | Jimsonweed | Morning glory | Pigweed | Velvetleaf | Barnyard Grass | Johnsongrass | Yellow Foxtail |
|---|---|---|---|---|---|---|---|---|---|---|---|---|---|---|
| $OCH_3$ | Cl | H | Cl | 36 | 75 | 90 | 100 | 100 | 50 | 100 | 95 | 90 | 85 | 90 |
| $OCH_3$ | $CF_3$ | H | $CCH_3$ | 36 | 85 | 100 | 85 | 80 | 50 | 100 | 90 | 100 | 95 | 100 |
| $OCH_3$ | Br | H | Br | 140 | 65 | 100 | no test | no test | 90 | no test | 95 | 90 | 85 | 98 |
| $OCH_3$ | Cl | $CH_3$ | Cl | 140 | 85 | 20 | 100 | no test | 75 | 80 | 95 | 0 | 0 | 70 |
| | | | | 36 | 0 | 0 | 90 | no test | 20 | 100 | 25 | 0 | 0 | 50 |
| $OCH_3$ | F | H | F | 140 | 90 | 100 | 100 | 100 | 60 | 100 | 85 | 90 | 75 | 100 |
| $SCH_3$ | Cl | H | Cl | 140 | 80 | 95 | 70 | 85 | 65 | 100 | 75 | 70 | 90 | 90 |
| $SCH_3$ | Br | H | Br | 310 | 85 | 100 | no test | no test | 80 | no test | 80 | 85 | 85 | 80 |

EXAMPLE 8

Soil Degradation Evaluation

A sandy clay loam soil from Davis, CA having a pH of about 7.3, a soil organic matter of about 1.6 percent, and consisting of about 50 percent sand, 26 percent silt, and 24 percent clay was employed. This soil was stored moist at about 13°–16° C. and was air dried and sifted in preparation for use. One hundred gram samples of this soil were placed in small plastic cups with no drain holes and treated with 20 ml of water (sufficient water to bring the soil to about 80 percent of its field capacity) containing the quantity of test compound required to give the desired application rate. The solutions were prepared by dissolving the test compounds in a 97:3 acetone-dimethyl sulfoxide mixture and diluting with water. The application rates were recorded as ppm in the soil and 0.1 ppm in the test is the equivalent of about 40 g/Ha. Enough cups were prepared to treat twelve sets of cups for each of three 3 incubation periods and each of five concentrations of each compound and for untreated controls. The cups were then capped with plastic lids containing an air hole about 3 mm in diameter and allowed to stand overnight at ambient temperature to equilibrate. Duplicate treatments were made for each frozen control, and each untreated control was then determined by adding together the ratings of the six replicates and dividing by six.

The percent of growth reduction was found for each compound at each concentration and each sampling time by applying the equation: 100 × (phytotoxicity index of treatment − phytotoxicity index of untreated control)/phytotoxicity index of untreated control. The loss of herbicidal activity for each compound at each sampling period was then determined by plotting the percentage of growth reduction figures against the log of the initial concentration in the soil in ppm and finding the $GR_{50}$ (the amount of compound required to be applied for a 50 percent reduction in root growth after the stated time period) for each incubated compound and each frozen control at each sampling time. This data was converted to percentage loss of effectiveness of the herbicide due to soil degradation by application of the equation: 100 × ($GR_{50}$ of incubated − $GR_{50}$ of frozen control)/$GR_{50}$ of incubated. The half-life for degradation in the soil was the determined by application of the standard first-order rate equation. The half-lives obtained at the various times were averaged to obtain the reported values. Half-lives under these conditions and using this method for the compounds of the present invention listed below were found to be less than 21 days.

5-Fluoromethyl-7-methoxy-N-(2,6-dichlorophenyl)-1,2,4-triazolo[1,5-a]pyrimidine-2-sulfonamide, 5-Fluoromethyl-7-methoxy-N-(2,6-dichloro-3-methylphenyl)-1,2,4-triazolo[1,5-a]pyrimidine-2-sulfonamide, 5-Fluoromethyl-7-methoxy-N-(2-methoxy-6-(trifluoromethyl)phenyl)-1,2,4-triazolo[1,5-a]pyrimidine-2-sulfonamide, 5-Fluoromethyl-7-methoxy-N-(2,6-difluorophenyl)-1,2,4-triazolo1,5-a]pyrimidine-2-sulfonamide 5-Fluoromethyl-7-methylthio-N-(2,6-dichlorophenyl)-1,2,4-triazolo1,5-a]pyrimidine-2-sulfonamide, and 5-Fluoromethyl-N-(2,6-difluorophenyl)-1,2,4-triazolo[1,5-a]pyrimidine-2-sulfonamide.

What is claimed is:

1. A compound of the formula

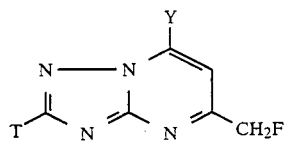

wherein

Y represents H, Cl, OH, $CH_3$, $C_2H_5$, or $OCH_3$, and

T represents HS, $(C_2-C_4)$alkylthio, benzylthio, or $ClSO_2$.

2. A compound of claim 1 wherein T represents HS or benzylthio.

3. A compound of claim 1 wherein T represents $ClSO_2$.

4. A compound of claim 1 wherein Y represents Cl, OH, or $OCH_3$.

5. A compound of claim 4: 2-benzylthio-5-fluoromethyl-7-hydroxy-1,2,4-triazolo1,5-a]pyrimidine.

6. A compound of claim 4: 2-benzylthio-5-fluoromethyl-7-chloro-1,2,4-triazolo1,5-a]pyrimidine.

7. A compound of claim 4: 5-fluoromethyl-7-chloro-1,2,4-triazolo[1,5-a]pyrimidine-2-sulfonyl chloride.

* * * * *